United States Patent
Sacurai et al.

(10) Patent No.: US 8,338,432 B2
(45) Date of Patent: Dec. 25, 2012

(54) DERIVATIVES OF 6,7-DIHYDRO-3H-OXAZOLO[3,4-A]PYRAZINE-5,9-DIONE AS PDE-5 INHIBITORS

(75) Inventors: Sérgio Luiz Sacurai, São Paulo (BR); Márcio Henrique Zaim, São Paulo (BR); Carlos Eduardo da Costa Touzarim, São Paulo (BR); Artur Franz Keppler, São Paulo (BR); Gilberto De Nucci, São Paulo (BR)

(73) Assignee: Biolab Sanus Farmaceutica Ltda., Vila Olimpia, Sao Paulo (BR)

( * ) Notice: Subject to any disclaimer, the term of this patent is extended or adjusted under 35 U.S.C. 154(b) by 0 days.

(21) Appl. No.: 13/196,363

(22) Filed: Aug. 2, 2011

(65) Prior Publication Data
US 2012/0040988 A1 Feb. 16, 2012

Related U.S. Application Data

(60) Provisional application No. 61/373,483, filed on Aug. 13, 2010.

(51) Int. Cl.
*A61K 31/4965* (2006.01)
(52) U.S. Cl. .................. 514/255.05; 544/350; 548/469; 549/434
(58) Field of Classification Search ............ 514/255.05; 544/350; 548/469; 549/434
See application file for complete search history.

(56) References Cited

FOREIGN PATENT DOCUMENTS
WO  WO 2012/019254  *  2/2012

OTHER PUBLICATIONS

Jordan, V. C. Nature Reviews: Drug Discovery, 2, 2003, 205.*
Vippagunta, et al. Advanced Drug Delivery Reviews, 48, 2001, 18.*

* cited by examiner

*Primary Examiner* — Douglas M Willis
(74) *Attorney, Agent, or Firm* — Arent Fox LLP

(57) ABSTRACT

A series of derivatives of 6,7-dihydro-3H-oxazolo[3,4-a]pyrazine-5,8-dione, mixtures thereof, their pharmaceutically acceptable salts, which are inhibitors of PDE-5, possessing vasodilatator properties and relaxing effects. In particular, compounds of formula (I), where $R_1$, $R_2$, $R_3$, and $R_4$ are defined herein, processes for the preparation of said compounds, pharmaceutical compositions containing them, as well as uses as inhibitors of the enzyme phosphodiesterase type 5 (PDE-5) in the treatment of the erectile dysfunction and PDE-5 inhibitor treatable disorders.

Formula (I)

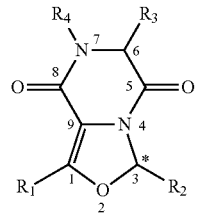

16 Claims, 3 Drawing Sheets

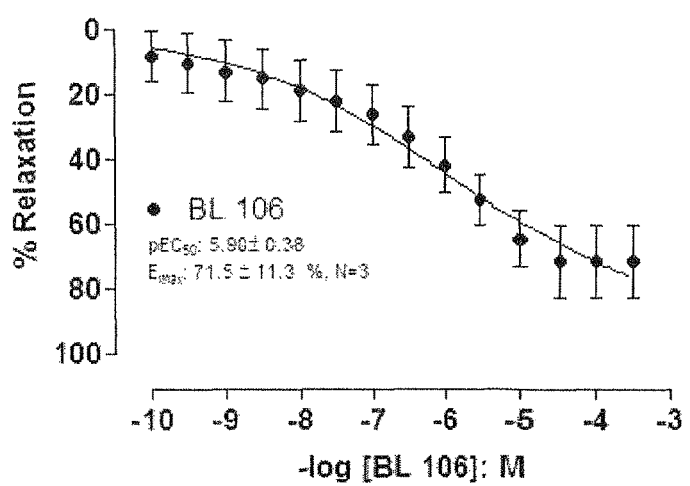
Figure 1. Concentration response curve to BL 106 in isolated urether from human. Data are the mean ± SEM, n=3 experiments.

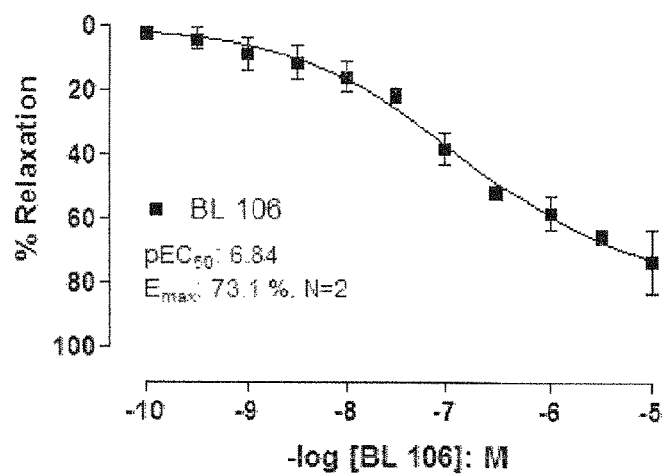
Figure 2. Concentration response curve to BL 106 in isolated pulmonary artery from rabbit.

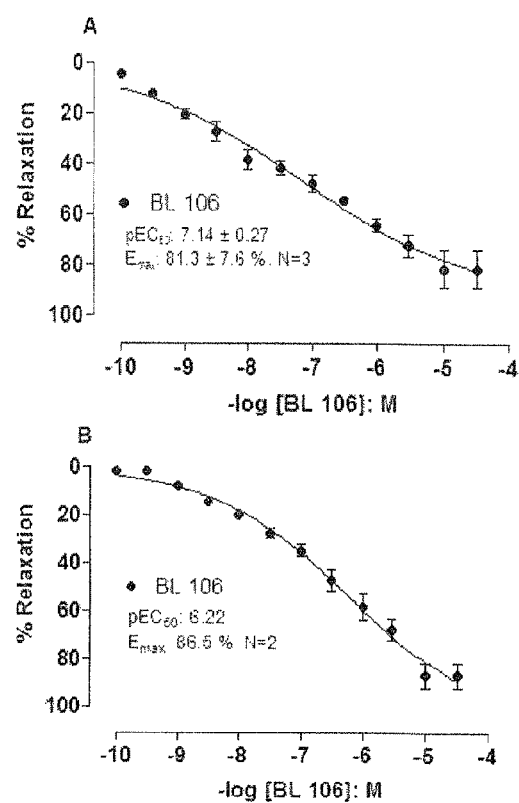
Figure 3. Concentration response curve to BL 106 in isolated corpus cavernosum from human (A) and rabbit (B). Data are the mean ± SEM, n=3 experiments.

DERIVATIVES OF 6,7-DIHYDRO-3H-OXAZOLO[3,4-A]PYRAZINE-5,9-DIONE AS PDE-5 INHIBITORS

FIELD OF THE INVENTION

The present invention describes a series of derivatives of 6,7-dihydro-3H-oxazolo[3,4-a]pyrazine-5,8-dione, mixtures thereof, their pharmaceutically acceptable salts, pharmaceutical compositions containing them, processes of their preparation, method of inhibiting the enzymes phosphodiesterases, their use as an inhibitor of the enzymes phosphodiesterases, and their use as an inhibitor of the enzyme phosphodiesterase of type 5 (PDE-5). In particular, the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

The present invention also describes a method of treatment of erectile dysfunction, tissue relaxation treatable disorders and/or conditions and PDE-5 inhibitor treatable disorders using derivatives of 6,7-dihydro-3H-oxazolo[3,4-a]pyrazine-5,8-dione, mixtures thereof (in any ratio) and/or their pharmaceutically acceptable salts. In particular, the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

BACKGROUND OF THE INVENTION

Before the appearance of the first oral treatment, male sexual impotence was treated by intracavernous injections and other means, due to, in particular, doubts stemming from adverse reactions that oral administration could cause in humans. Papaverine and pentoxifylline, for example, were used in the treatment of erectile dysfunction by intracavernous injections. Other means of treatment, less efficient, were, for example, psychotherapies and surgical implants.

Oral treatment is most acceptable by man, and it emerged from clinical research using inhibitors of cGMP-PDE, more specifically, PDE-5. The precursor of these compounds was 5-[2-ethoxy-5-(4-methylpiperazinylsulfonyl)phenyl]-1-methyl-3-n-propyl-1,6-dihydro-7H-pyrazolo[4,3-d]pyrimidin-7-one, or sildenafil, with vasodilator properties and potentiates the effects of nitric oxide. Sildenafil is the active ingredient of the medicine Viagra®.

Later, other inhibitor compounds of PDE-5 were developed and are cited in numerous publications of technical literature, as well as patent publications, such as vardenafil, the active ingredient of the medicine Levitra®, and tadalafil, the active ingredient of the medicine Clalis®.

The compounds of the present invention, the derivatives of 6,7-dihydro-3H-oxazolo[3,4-a]pyrazine-5,8-dione, are also inhibitors of the enzyme phosphodiesterase type 5 (PDE-5).

DESCRIPTION OF THE INVENTION

It is, therefore, the objective of the present invention to provide new derivative compounds of 6,7-dihydro-3H-oxazolo[3,4-a]pyrazine-5,8-dione, mixtures thereof (in any ratio), their pharmaceutically acceptable salts, pharmaceutical compositions containing them, that are effective in the treatment of erectile dysfunction, said compounds being tissue relaxants, and/or inhibitors of the enzymes phosphodiesterases possessing vasodilatador properties and relaxing effects, particularly inhibitors of PDE-5. In particular, the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

It is also the objective of the present invention to provide processes preparation of derivative compounds of 6,7-dihydro-3H-oxazolo[3,4-a]pyrazine-5,8-dione, and mixtures thereof. In particular, the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

Furthermore, it is the objective of the present invention to provide pharmaceutical compositions comprising an effective amount of one of the derivatives of 6,7-dihydro-3H-oxazolo[3,4-a]pyrazine-5,8-dione or mixes thereof (in any ratio) or their pharmaceutically acceptable salts, and pharmaceutically acceptable excipients. In particular, pharmaceutical compositions comprising the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

An additional objective of the present invention is to provide a medicament comprising a therapeutically effective amount of one of the derivatives of 6,7-dihydro-3H-oxazolo[3,4-a]pyrazine-5,8-dione or mixtures thereof (in any ratio) or their pharmaceutically acceptable salts. In particular, medicaments comprising the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

Another objective of the present invention is the use of one of the derivatives of 6,7-dihydro-3H-oxazolo[3,4-a]pyrazine-5,8-dione, or mixtures thereof (in any ratio), or their pharmaceutically acceptable salts, for curative and/or prophylactic treatment of erectile dysfunction, tissue relaxation treatable disorders and/or conditions, and PDE-5 inhibitor treatable disorders in animal. In particular, the derivative (R)-3-(1,3-benzodioxol-5-yl)-1-(1H-indol-3-yl)-7-methyl-6,7-dihydro[1,3]oxazolo[3,4-a]pyrazine-5,8-dione, its enantiomer (S)-3-(1,3-benzodioxol-5-yl)-1-(1H-indol-3-yl)-7-methyl-6,7-dihydro[1,3]oxazolo[3,4-a]pyrazine-5,8-dione, and/or mixtures thereof (in any ratio).

BRIEF DESCRIPTION OF THE DRAWINGS

FIG. 1 shows the relaxing effects of compound 2 (BL 106) on human isolated urether tissue.

FIG. 2 shows the relaxing effects of compound 2 (BL 106) on rabbit isolated pulmonary artery tissue.

FIG. 3 shows the relaxing effects of compound 2 (BL 106) on human isolated corpus cavernosum tissue (FIG. 3A) and rabbit isolated corpus cavernosum tissue (FIG. 3B).

DETAILED DESCRIPTION OF THE INVENTION

The present invention describes derivatives of 6,7-dihydro-3H-oxazolo[3,4-a]pyrazine-5,8-dione with structures represented in formula (I):

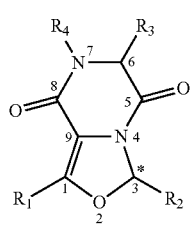

(I)

and salts and solvates (for example, hydrates) thereof, where:
$R^1$ represents an aromatic group, condensed group or not, (optionally substituted with $R^B$ in one or more positions), a heteroaromatic group containing one or more heteroatoms or indol groups (optionally substituted with $R^B$ in one or more positions), $C_{1-6}$ alkenylcarbonyl (optionally substituted with $R^B$ in one or more positions), bicyclic aromatic (optionally substituted with $R^B$ in one or more positions), or bicyclic heteroaromatic, containing one or heteroatoms (optionally substituted with $R^B$ in one or more positions);
$R^B$ represents halogen, hydroxyl, nitrogen, cyano, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl;
$R^2$ represents an aromatic group containing one or heteroatoms, or bicyclic aromatic or heteroaromatic containing one or more heteroatoms or methylene-3,4-dioxyphenyl groups;
$R^3$ represents hydrogen, halogen, $C_{1-6}$ haloalkyl, $C_{1-3}$ heteroalkyl, or $C_{1-3}$ alkyl;
$R^4$ represents hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl.

In one aspect, "$C_{2-6}$ alkenylcarbonyl" of $R^1$ represents one or more alkenyl groups, containing from 2 to 6 carbon atoms, conjugated or not with a carbonyl group.

In one aspect, "aryl" of $R^B$ and $R^4$, e.g., aryl$C_{1-3}$ alkyl, represents a phenyl group or phenyl substituted one or more times (e.g. 1, 2 or 3) by halogen, $C_{1-6}$ alkyl, $C_{1-6}$ alkoxyl or methylenedioxyl. In another aspect, "heteroaryl" of $R^B$ and $R^4$, e.g., hetroaryl$C_{1-3}$ alkyl, represents a furil group or pyridyl, optionally substituted one or more times with halogen, $C_{1-6}$ alkyl or $C_{1-6}$ alkoxyl. In another aspect, "$C_{3-8}$ cycloalkyl" of $R^B$ and $R^4$, e.g., $C_{3-8}$ cycloalkyl$C_{1-3}$ alkyl, represents a monocyclic ring containing from 3 to 8 carbon atoms. Examples of cycloalkyl rings include $C_{3-6}$ cycloalkyl rings: cyclopropyl, cyclobutyl, cyclopentyl and cyclohexyl.

The term "alkyl" can represent an alkyl chain or branched alkyl chain. For example, the $C_{1-4}$ alkyl group can represent methyl, ethyl, n-propyl, i-propyl, n-butyl, s-butyl and t-butyl. The term "alkenyl" includes alkenyl groups of straight and branched chains, e.g., vinyl and allyl groups. The term "alkynyl" includes alkynyl groups of straight and branched chains, e.g., acetylene. The term "halogen" can represent atoms of fluorine, chlorine, bromine or iodine. The term "halo $C_{1-6}$ alkyl" can represent an alkyl group containing from one to six carbon atoms, substituted with one or more (e.g. 1, 2 or 3) atoms of halogen.

The compounds of formula (I) can contain one or more asymmetrical centers, thus existing as enantiomers and/or diastereomers. For example, in formula (I), a chiral center is indicated with an asterisk. Accordingly, the invention includes one or more enantiomers, and mixtures thereof (in any ratio).

The compounds of formula (I) can exist with different tautomeric forms, and the invention includes one or more tautomeric forms, and mixtures thereof (in any ratio).

Pharmaceutically acceptable salts of the compounds of formula (I), which possess a basic center, are formed by the addition of pharmaceutically acceptable acids. Some examples include salts of hydrochloride, hydrobromide, sulfate or bisulfate, phosphate or hydrogen phosphate, acetate, benzoate, succinate, fumarate, maleate, lactate, citrate, tartarate, gluconate, methanesulfonate, benzenesulfonate and p-toluenesulfonate. The compounds of formula (I) can be used in pharmaceutically acceptable metal salts, in particular salts of alkaline metals, with bases. For example, salts of sodium and potassium.

In one embodiment, the compounds of this invention have a structure represented in formula (I), where $R^1$ represents an indol group, $R^2$ represents an 3,4-methylenedioxyphenyl group, $R^3$ represents hydrogen and $R^4$ represents a methyl group. In a preferred embodiment, the compounds of this invention are (R)-3-(benzo[d][1,3]dioxol-5-yl)-1-(1H-indol-3-yl)-7-methyl-6,7-dihydro-3H-oxazolo[3,4-a]pyrazine-5,8-dione, and/or its enantiomer (S)-3-(benzo[d][1,3]dioxol-5-yl)-1-(1H-indol-3-yl)-7-methyl-6,7-dihydro-3H-oxazolo[3,4-a]pyrazine-5,8-dione.

The compound (R,S)-3-(1,3-benzodioxol-5-yl)-1-(1H-indol-3-yl)-7-methyl-6,7-dihydro[1,3]oxazolo[3,4-a]pyrazine-5,8-dione (2), according to the present invention, can be prepared from the reaction of compound 1 in the presence of methylamine, using ethanol as solvent, according to Scheme 1:

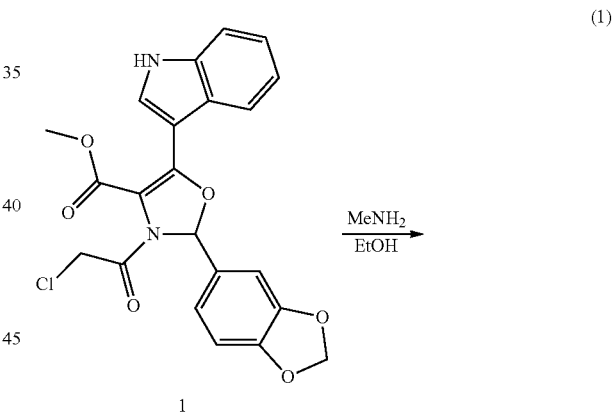

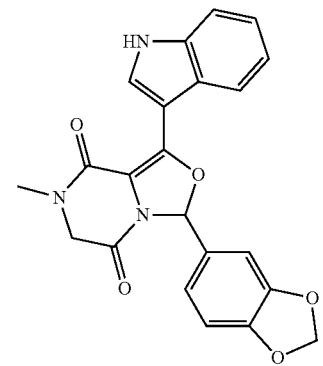

An alternative approach for the preparation of compound 2 is via the reaction of 3 with acid in ethanol, according to Scheme 2:

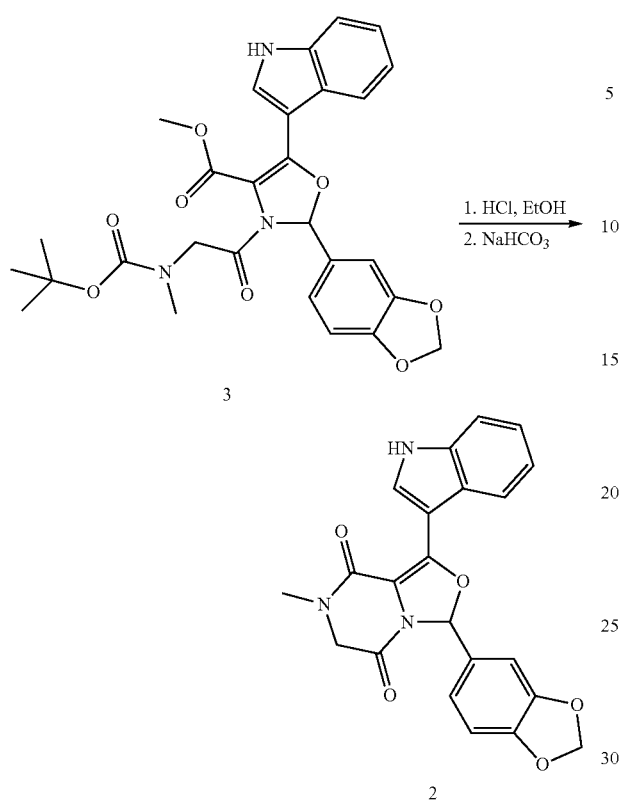

3

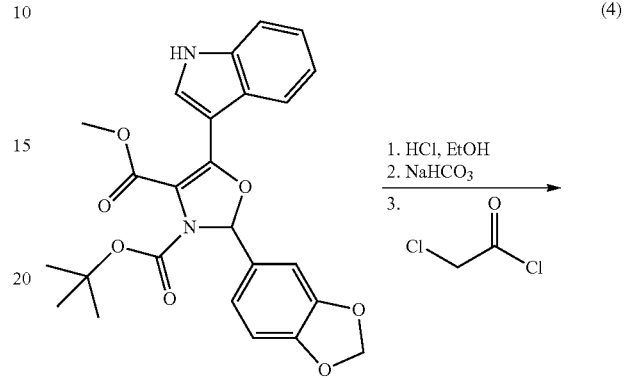

2

Compound 1 can be prepared according to Scheme 3:

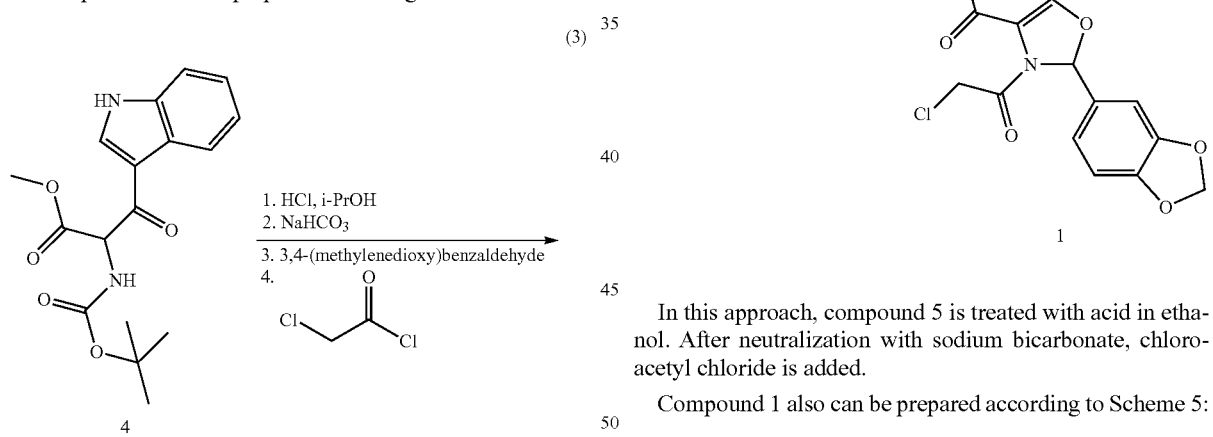

Compound 4 is treated with acid in isopropanol. After neutralization with sodium bicarbonate, 3,4-(methylendioxy)benzaldehyde is added. The last step of this approach is addition of chloroacetyl chloride.

Alternatively, compound 1 can be prepared according to Scheme 4:

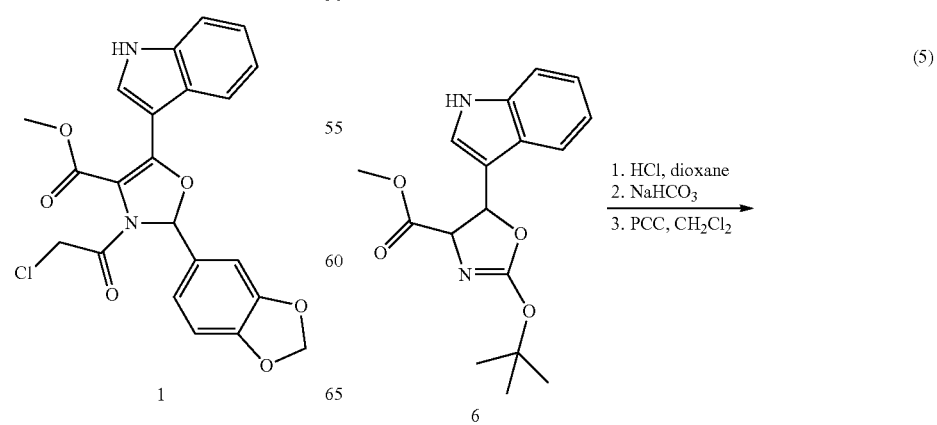

In this approach, compound 5 is treated with acid in ethanol. After neutralization with sodium bicarbonate, chloroacetyl chloride is added.

Compound 1 also can be prepared according to Scheme 5:

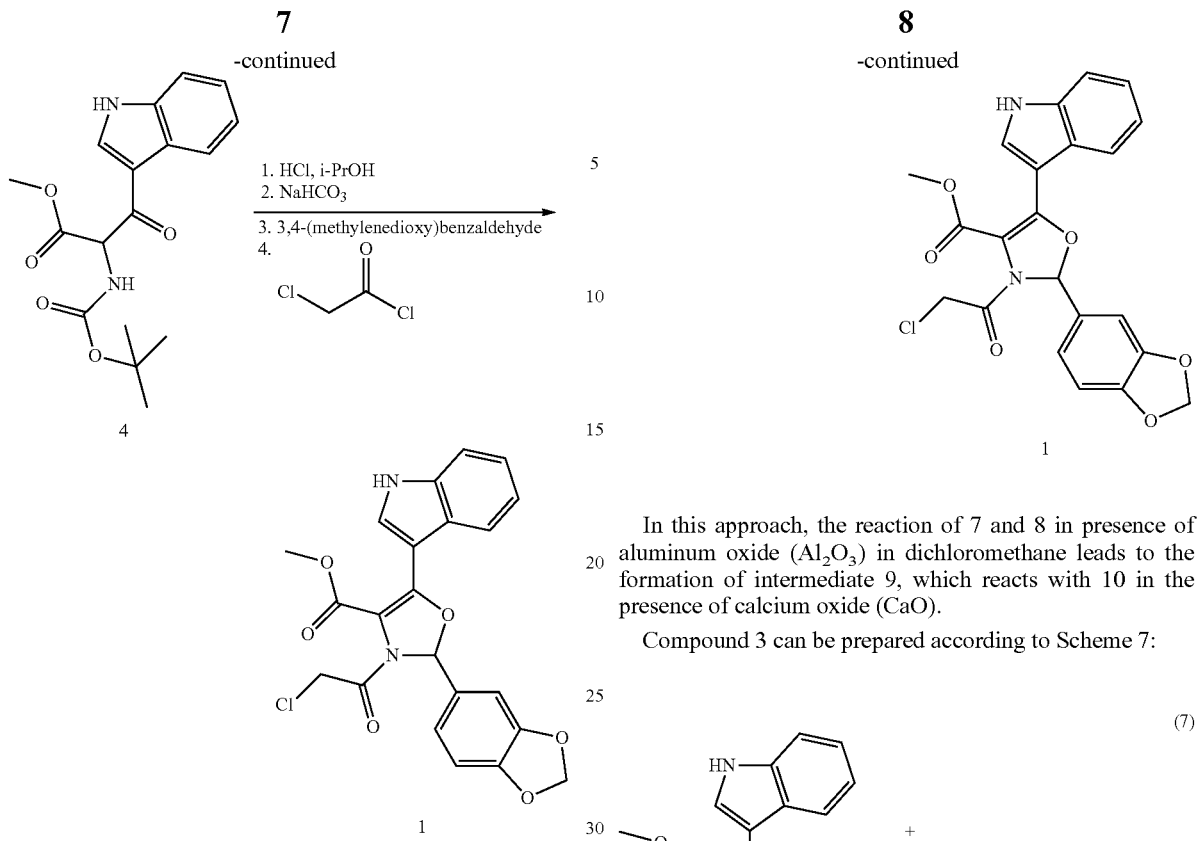

In this approach, compound 6 is treated with acid in dioxane. After neutralization with sodium bicarbonate, an oxidation reaction is made with pyridine chlorochromate (PCC), leading to formation of intermediate 4, that is treated with acid in isopropanol. After neutralization with sodium bicarbonate, 3,4-(methylendioxy)benzaldehyde is added. The last step of this approach is addition of chloroacetyl chloride.

Another approach for preparation of compound 1 is given in Scheme 6:

(6)

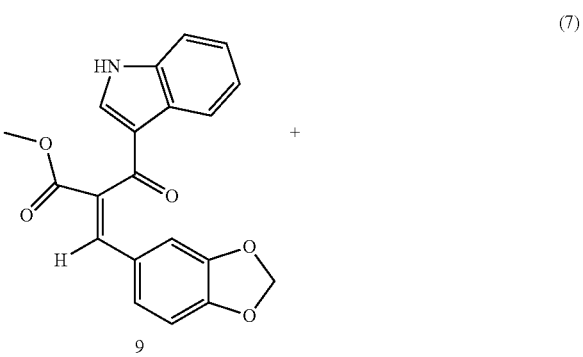

In this approach, the reaction of 7 and 8 in presence of aluminum oxide (Al$_2$O$_3$) in dichloromethane leads to the formation of intermediate 9, which reacts with 10 in the presence of calcium oxide (CaO).

Compound 3 can be prepared according to Scheme 7:

(7)

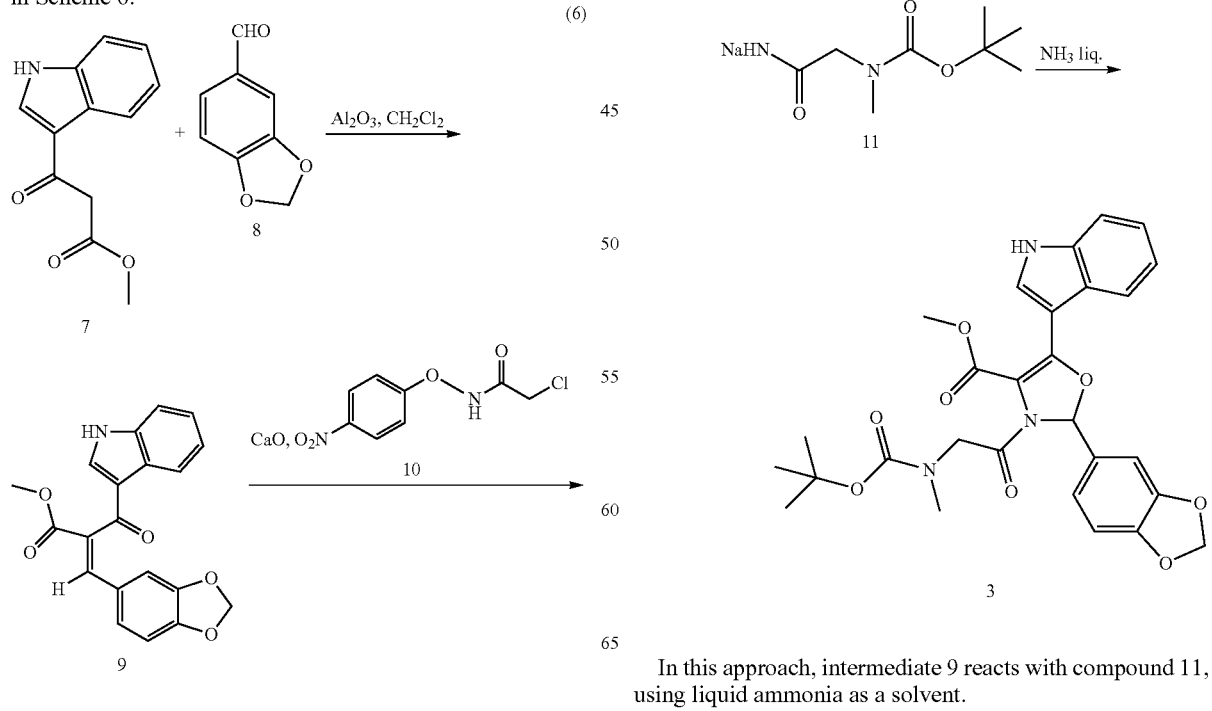

In this approach, intermediate 9 reacts with compound 11, using liquid ammonia as a solvent.

Alternatively, compound 3 can be prepared according to Scheme 8:

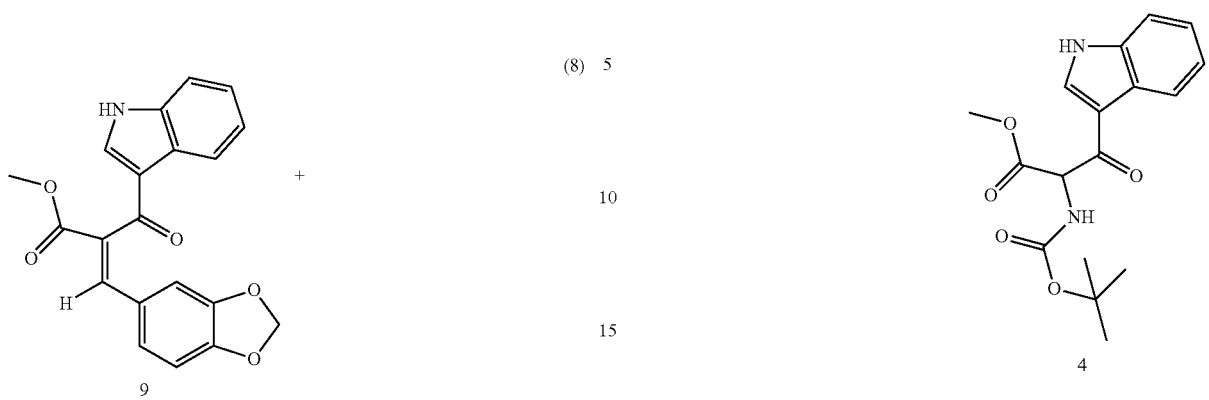

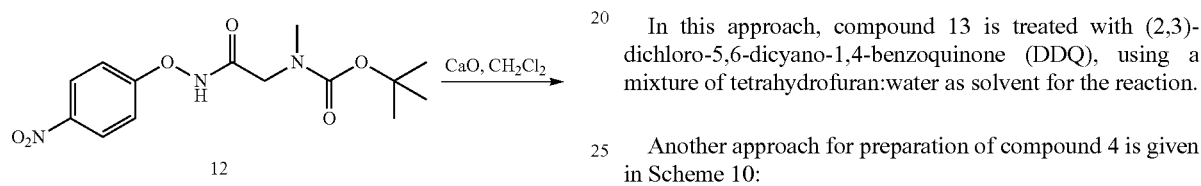

In this approach, in the presence of calcium oxide (CaO), intermediate 9 reacts with compound 12.

Compound 4 can be prepared according to Scheme 9:

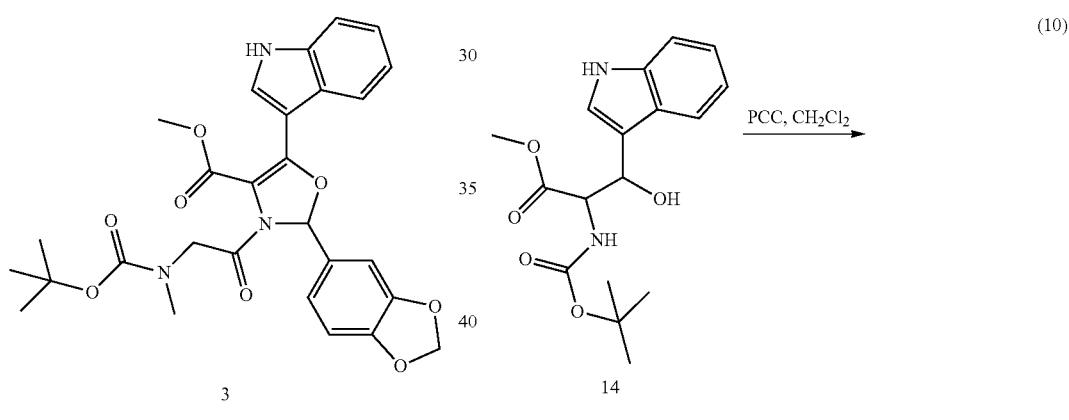

In this approach, compound 13 is treated with (2,3)-dichloro-5,6-dicyano-1,4-benzoquinone (DDQ), using a mixture of tetrahydrofuran:water as solvent for the reaction.

Another approach for preparation of compound 4 is given in Scheme 10:

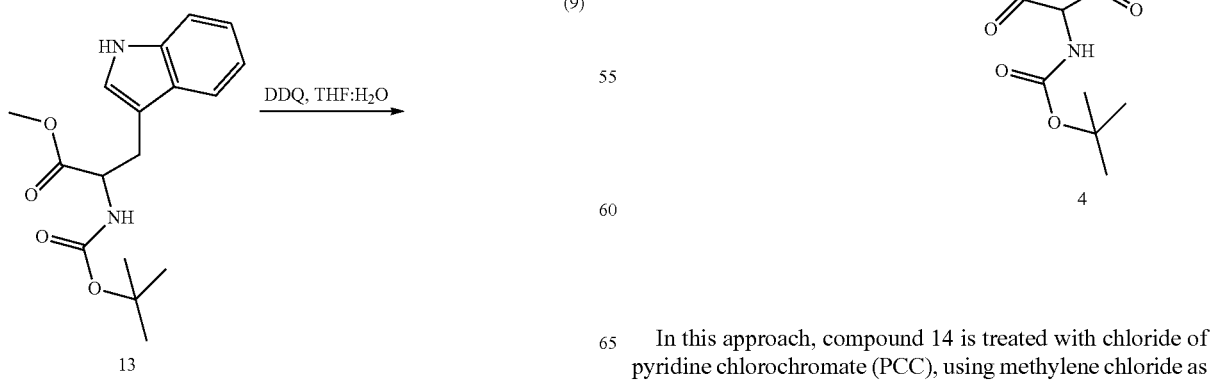

In this approach, compound 14 is treated with chloride of pyridine chlorochromate (PCC), using methylene chloride as solvent for the reaction.

Compound 5 can be prepared according to Scheme 11:

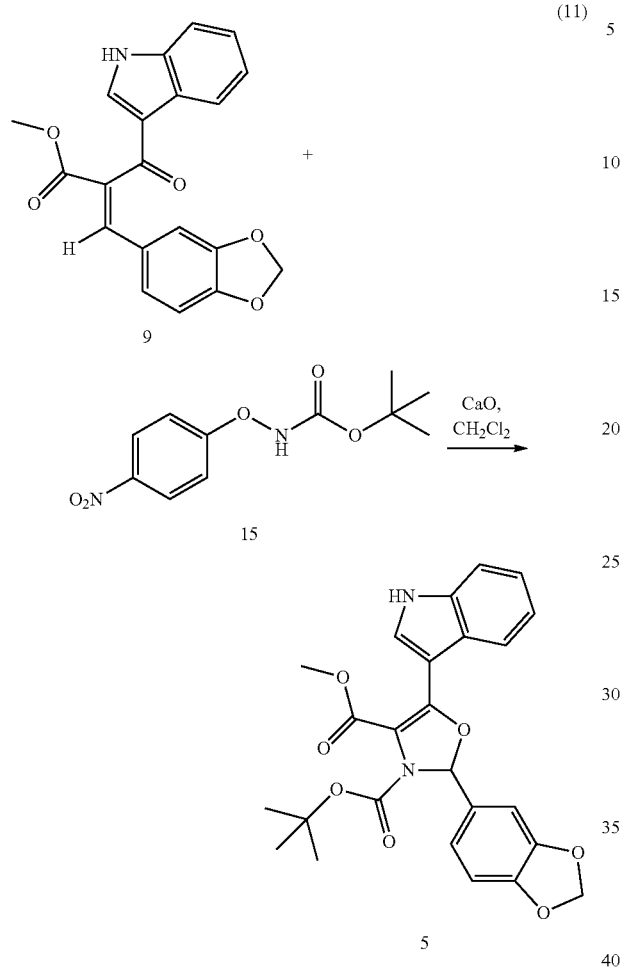

In this approach, in the presence of calcium oxide (CaO), intermediate 9 reacts with compound 15.

Alternatively, compound 5 can be prepared according to Scheme 12:

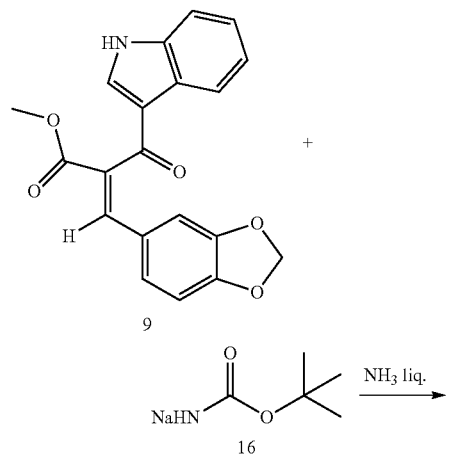

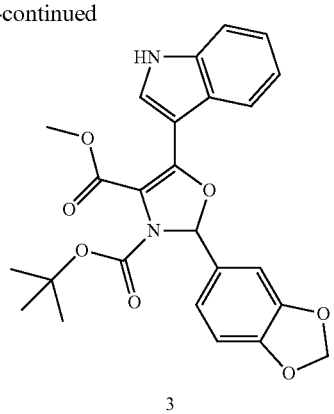

In this approach, intermediate 9 reacts with compound 16, using liquid ammonia as solvent.

Compound 6 can be prepared according to Scheme 13:

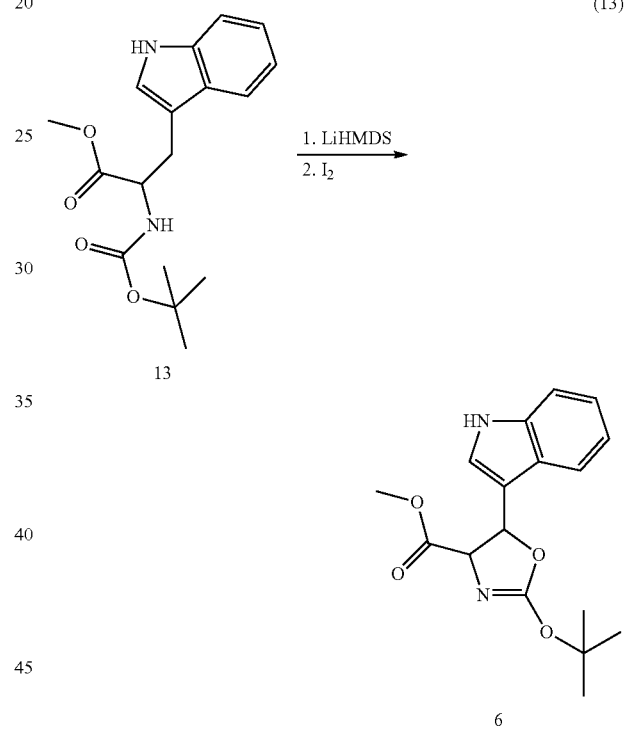

In this approach, compound 13 is treated with lithium hexamethyldisilazide (LiHDMS). The last step of this approach is iodine addition ($I_2$).

Compound 14 can be prepared according to Scheme 14.

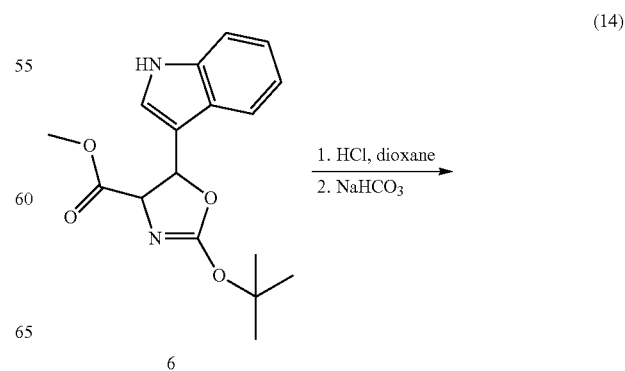

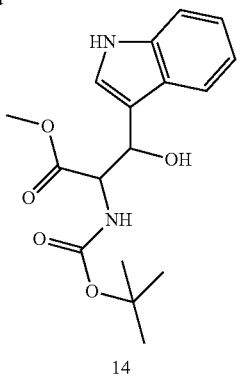

14

In this approach, compound 6 is treated with acid in dioxane.

All compounds containing the carboxymethyl group, particularly 1, 3, 5 and 7 can be prepared from (their) derivatives containing the nitrile group, e.g., according to Scheme 15.

thereof. In another embodiment, the pharmaceutical composition further comprises one or more compounds that treat erectile dysfunction or the PDE-5 inhibitor treatable disorder.

In one embodiment, the pharmaceutical composition is administered with a second pharmaceutical composition comprising other PDE-5 inhibitors, for example sildenafil, vardenafil and tadalafil; or a pharmaceutically acceptable salt thereof. In another embodiment, said second pharmaceutical composition comprises one or more compounds that treat erectile dysfunction or the PDE-5 inhibitor treatable disorder. The administration may be co-administration or sequential administration.

Pharmaceutical compositions may be prepared by methods well known in the state of the art. Appropriately, Remington's Pharmaceutical Sciences or similar information sources may be used to prepare a suitable formulation according to the invention.

Pharmaceutical compositions for oral administration may be presented as discrete units such as capsules, tablets, effervescent tablets, chewable tablets, pills, powders, granules and

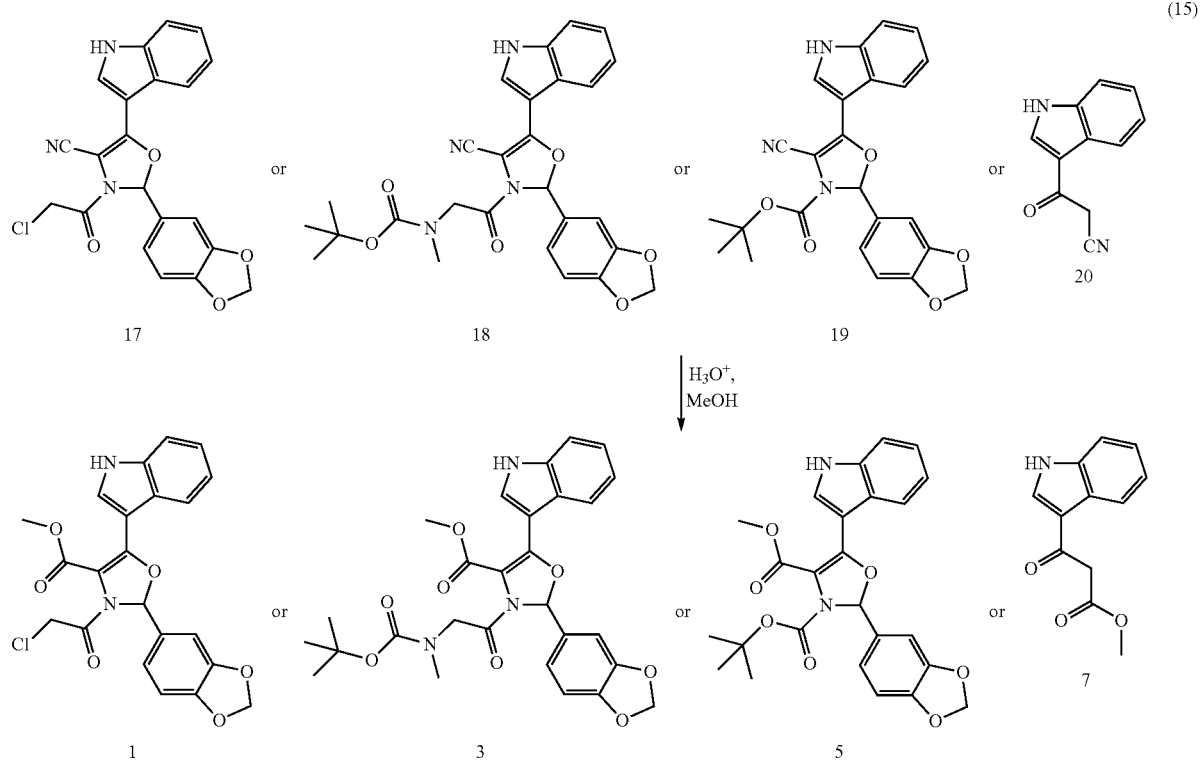

(15)

For example, compound 17 is treated with acid in methanol. This approach can also be used, individually, with compounds 18, 19 and 20 in order to prepare intermediates 3, 5 and 7 respectively.

The present invention also provides a pharmaceutical composition, e.g. an appropriate dosage form, wherein said composition comprises an effective amount of one or more compounds of formula (1) or a pharmaceutically acceptable salt thereof, and a pharmaceutically acceptable excipient.

In one embodiment, the pharmaceutical composition further comprises other PDE-5 inhibitors, such as sildenafil, vardenafil and tadalafil; or a pharmaceutically acceptable salt gels or similar pharmaceutical forms. Other oral formulation forms include suspensions or emulsions in an aqueous or non-aqueous carrier.

In solid dosage forms, the compounds of formula (I) can be admixed with a pharmaceutically acceptable carrier comprising at least one component selected from the group comprising diluents, binders, disintegrants, lubricants, coloring agents, and flavoring agents. Exemplary inert diluents are calcium carbonate, calcium phosphate-dibasic, calcium phosphate-tribasic, calcium sulfate, cellulose-microcrystalline, cellulose powdered, dextrates, dextrins, cyclodextrins, dextrose excipients, fructose, kaolin, lactitol, lactose, mannitol, sorbitol, starch, starch pregelatinized, sucrose, sugar compressible, and sugar confectioners. As binders may be used one or more substances, e.g., methyl cellulose, hydroxypropyl cellulose, hydroxypropyl methyl cellulose, polyvinylpyrrolidone, gelatin, gum arabic, ethyl cellulose, polyvinyl alcohol, pullulan, pregelatinized starch, agar, tragacanth, sodium alginate, propylene glycol, and alginate. As disintegrant may be used one or more substances selected from low substituted hydroxypropyl cellulose, carboxymethyl cellulose, calcium carboxymethyl cellulose, sodium carboxymethyl cellulose, croscarmellose sodium, starch, crystalline cellulose, hydroxypropyl starch, and partially pregelatinized starch, and croscarmellose sodium. Exemplary lubricants are stearic acid, magnesium stearate, calcium stearate, talc, hydrogenated castor oil, and sucrose.

In the case of capsules, tablets, effervescent tablets, and pills, the dosage forms can also comprise buffering agents. Soft gelatin capsules can be prepared to contain a mixture of the compounds of formula (I) and vegetable oil. Hard gelatin capsules may contain granules of the compounds of formula (I) in combination with a solid, pulverulent carrier such as, lactose, saccharose, sorbitol, mannitol, potato starch, corn starch, amylopectin, cellulose derivatives of gelatin. In addition, tablets and pills can be prepared with enteric coatings.

In one embodiment, the dosage forms are a controlled/retarded/modulated release type, which are based on carriers or matrices including, but not being limited to, biocompatible polymers, pharmaceutically acceptable polymeric matrices, liposomes, PEG-liposomes, or a cyclodextrin or a cyclodextrin derivative matrix.

Pharmaceutical compositions may be administered by a variety of administration routes, including, but not being limited to, oral, intracavernosal injection, topically and transdermally delivered through the skin into various sites or parenteral routes. The particular mode selected will depend on the compounds present in the composition, the severity of the erectile dysfunction, tissue relaxation treatable disorders and/or conditions, or PDE-5 inhibitor treatable disorder being treated and the dosage required for therapeutic efficacy. Preferably, the compositions of the invention are in oral administration form because of convenience of the patient and the dosing schedule.

Tissue relaxants have been used to promote relaxation on various tissues to treat or act as adjuvant of the treatment, procedure or surgery related with lithiasis (Korkes, F. et al, J Bras Nefrol. (2009) 31(1): 55), prostate enlargement (e.g., benign prostatic hyperplasia, prostatitis) (WO 9911279) and urether constriction (Van der werf et al, BJU International (2002) 90:588). Other tissue relaxation treatable disorders and/or conditions are known and described in the art.

PDE-5 inhibitors have been used to block cGMP degradation to prolong the effects of nitric oxide (NO) on various tissues, e.g., to maintain NO-induced relaxation of airways and vessels (Barnes, P. J., et al., (1995), and to maintain NO-induced protection of tissue (Duffin, R., et. al., Br J. Pharmacol. (2008) 153(4): 623). Such actions on tissues have been shown beneficial for treatment of several disorders—herein, PDE-5 inhibitor treatable disorders—including pulmonary hypertension (commercially treated with sildenafil citrate); bronchitis, chronic asthma, hypertension (EP 758653, U.S. Pat. No. 7,569,572); Raynaud's phenomenon (Ghofrani H. A., et. al., Nat Rev Drug Discov. 2006, 5:689); commencing right-heart failure (Ghofrani et al. (2003) AJRCCM 167(8): 1139); neurogenesis and functional recovery after stroke (Zhang et al. (2002) Stroke 33: 2675-2680); coronary artery relaxation (Halcox et al. (2002) J Am Coll Cardiol 40: 1232); female sexual arousal disorders (Nehra et al. (2001) World J Urol. 19(1): 115); angina and congestive heart failure (Reffelmann et al., Circ. (2003) 108(2): 239). Other PDE-5 inhibitor treatable disorders are known and described in the art.

A therapeutically effective amount for treatment of erectile dysfunction is one that is sufficient to achieve improvement in erectile function or an alleviation of the symptoms of erectile dysfunction, or even to restore the erectile capacity. A therapeutically effective amount for treatment of PDE-5 inhibitor treatable disorders is one that is sufficient to achieve improvement in said disorder or an alleviation of the symptoms of said disorder. Effective amounts will depend on the specific condition being treated and the severity thereof; individual patient characteristics, including age, physical condition, size and weight; concurrent treatment; and the mode of administration. These factors are well known to those skilled in the art and can be established without undue experimentation. Generally, doses of compounds of formula (I) will range from about 0.01 mg/kg body weight per day to 100 mg/kg body weight per day, preferably from 0.1 mg/kg body weight per day to 10 mg/kg body weight per day. Multiple doses per day may be contemplated to achieve appropriate systemic levels of active ingredients present in the composition of the invention.

The following Examples describe the present invention in more detail. It should be noted that the invention is not limited by the following description.

Example 1

Preparation of Compound 2, (R,S)-3-(1,3-benzodioxol-5-yl)-1-(1H-indol-3-yl)-7-methyl-6,7-dihydro[1,3]oxazolo[3,4-a]pyrazine-5,8-dione Preparation of Intermediate Compound 4

To a solution of DDQ (228.0 g; 1.0 mol) in a mixture 1000 mL of THF:$H_2O$ (9:1), was added methyl 2-[(tert-butoxycarbonyl)amino]-3-(1H-indol-3-yl)propanoate (80.0 g; 0.251 mol). The reaction mixture was mixed for 3 hours. Additional aliquots of DDQ were added until all the starting material was consumed (TLC). Afterwards, the reaction mixture was washed with a saturated solution of $NaHCO_3$ and the product was extracted with methylene chloride. The organic phases were combined and dried with $MgSO_4$. The solvent partially was removed and to this mixture was added 3 g of activated carbon. This mixture was mixed for 30 minutes and, after equilibrating to ambient temperature, was filtered. The solvent was removed by rotoevaporation until dryness. The resulting oil was heat solubilized in acetone (70.0 mL). The solution was cooled and placed in ice bath, leading to the precipitation of methyl 2-[(tert-butoxycarbonyl)amino]-3-(1H-indol-3-yl)-3-oxopropanoate, which was filtered and dried in a heater at 60° C.

Preparation of Intermediate Compound 1

To a suspension of methyl 2-[(tert-butoxycarbonyl)amino]-3-(1H-indol-3-yl)-3-oxopropanoate (6.23 g; 19.0 mmol) 4 in 200 mL of isopropanol, was added 2.0 mL of 36% HCl. The reaction mixture was mixed for 3 hours. Additional aliquots of 36% HCl were added until all the starting material was consumed. After completion of the reaction, the reaction mixture was cooled to ambient temperature. Aliquots of $NaHCO_3$ were added to neutralize the solution. 3,4-(Methylendioxy)benzaldehyde (2.86 g; 19 mmol) was then added to the solution and the resultant reaction mixture was mixed under magnetic agitation for 24 hours, leading to the precipitation of methyl 2-[(E)-(1,3-benzodioxol-5-ylmethylidene)amino]-3-(1H-indol-3-yl)-3-oxopropanoate, which was filtered and dried in a heater at 60° C.

Methyl 2-[(E)-(1,3-benzodioxol-5-ylmethylidene)amino]-3-(1H-indol-3-yl)-3-oxopropanoate (5.46 g; 15.0 mmol) was added to a solution of pyridine (10 mL) in 50 mL of dry methylene chloride. This suspension was mixed under magnetic agitation with a drying tube of $CaCO_3$ for 30 minutes. Chloroacetyl chloride (2.3 mL; 30.0 mmol) was dissolved in 2.5 mL of dry methylene chloride. This solution was added drop wise to the reaction mixture, over a period of 30 minutes. After an additional period of 3 hours, 100 mL of a saturated aqueous solution of $CuSO_4$ was added to the reaction mixture. The organic phase was extracted in a separation funnel and isolated. The aqueous phase was washed with 50 mL of methylene chloride and organic phase was isolated. The organic phases were combined. This procedure of washing was repeated two more times. The organic phase was washed with a saturated aqueous solution of NaCl. The organic phase was isolated and dried with $MgSO_4$. The solvent was removed by rotoevaporation, leading to the isolation of methyl 3-(chloroacetyl)-5-(1H-indol-3-yl)-2-phenyl-2,3-dihydro-1,3-oxazole-4-carboxylate 1.

Preparation of Compound 2

To a solution of methyl 3-(chloroacetyl)-5-(1H-indol-3-yl)-2-phenyl-2,3-dihydro-1,3-oxazole-4-carboxylate (5.46 g; 12.4 mmol) 1 in 100 mL of ethanol, was added 10 mL of an aqueous solution of 40% methylamine. This reaction mixture was mixed under magnetic agitation for 24 hours, leading to the precipitation of (R,S)-3-(1,3-benzodioxol-5-yl)-1-(1H-indol-3-yl)-7-methyl-6,7-dihydro[1,3]oxazolo[3,4-a]pyrazine-5,8-dione 2. The obtained product presented the following characteristics: M.P. 279-281° C. HRMS (EI): m/z cal. for $[C_{22}H_{18}N_3O_5]$ 404, 1246. found: 404, 1239. IV (KBr): 3322, 1647, 1613, 1467 $cm^{-1}$. NMR $^1H$ (300 MHz, DMSO-$d_6$): $\delta$=11.87 (s, 1H); 9.00 (s, 1H); 7.87 (d, 1H, J=9.0 Hz); 7.48 (d, 1H, J=9.0 Hz); 7.14 (m, 5H); 7.00 (d, 1H, J=9.0 Hz); 6.06 (s, 2H); 4.20 (s, 2H); 2.94 (s, 3H). NMR $^{13}C$ (125 MHz, DMSO-$d_6$): $\delta$=158.3; 156.7; 148.2; 147.5; 147.3; 135.7; 130.9; 130.7; 125.1; 122.0; 121.2; 120.4; 120.2; 112.0; 108.1; 106.4; 104.7; 102.2; 101.3; 90.1; 52.7; 32.2.

Example 2

Effect of Compound 2 on Human Corpus Cavernosum and Urether, and Rabbit Corpus Cavernosum and Pulmonary Artery Tissue Human corpus cavernosum and urether were obtained from discarded tissues from surgeries, which were placed in ice-cold Krebs solution for rapid transport to the laboratory.

Male New Zealand White rabbits (2-2.5 kg) were used for penis and pulmonary artery tissues, which were excised and transferred to ice-cold Kreb's solution. Two strips and four rings were obtained from each corpus cavernosum (CC) and pulmonary artery, respectively.

Isometric Tension Recording

Cavernosal strips, pulmonary artery, and urether were mounted in 10 ml organ chambers containing Kreb's solution at 37° C., pH 7.4 continuously bubbled with a mixture of 95% $O_2$ and 5% $CO_2$. The tissues were stretched to a resting force of 5 mN and allowed to equilibrate for 60 min. Changes in isometric force were recorded using a PowerLab 4/30 data acquisition system (Chart software, version 7.0; ADInstruments, Colo. Springs, Colo.). Cumulative concentration-response curves to compound 2 (named BL 106 in FIGS. 1, 2 and 3) (0.001-10 µM) were obtained in cavernosal strips, pulmonary artery rings, and urether contracted with noradrenaline (NOR 10 µM) (Sigma, St. Louis, Mo.). Concentration response curves to compound 2 (denoted BL 106 in FIGS. 1, 2 and 3) were constructed for each sample. For pulmonary artery, concentration response curves to compound 2 were also constructed in the presence or absence of the soluble guanylate cyclase inhibitor 1H-[1,2,4]Oxadiazolo[4,3-a]quinoxalin-1-one (ODQ 10 µM) (Sigma, St. Louis, Mo.). Control rings (treated with 40 mM DMSO) were also ran in parallel with experimental strips and rings.

Relaxation of Human Urether

Noradrenaline caused a sustained contraction in the human urether tissue. Compound 2 (BL 106) (0.0001-1 µM) produced concentration dependent relaxations in urether tissue (pEC50: 6.29 and Emax 49%, n=3) (FIG. 1).

Relaxation of Rabbit Pulmonary Artery

Noradrenaline (3 or 10 µM) caused a sustained contraction in the rabbit pulmonary artery (17.4 mN). The compound 2 (BL 106) (0.001-10 µM) produced concentration-dependent relaxations in pulmonary artery rings (pEC50: 6.23 [588 nM] and Emax 62%, n=3) (FIG. 2).

Relaxation of Human Corpus Cavernosum

Noradrenaline caused a sustained contraction in the human corpus cavernosum. The compound 2 (BL 106) (0.0001-1 µM) produced concentration-dependent relaxations in corpus cavernosum (pEC50: 7.65 and Emax 71%, n=3) (FIG. 3A).

Relaxation of Rabbit Corpus Cavernosum

Noradrenaline (3 or 10 µM) caused a sustained contraction in rabbit corpus cavernosum (13.8 mN). Compound 2 (BL 106) produced concentration dependent relaxations in corpus cavernousum (pEC50: 5.92 [1.2 µM] and Emax: 91%, n=3) (FIG. 3B).

The invention claimed is:

1. A compound of formula (I):

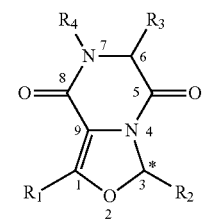

or pharmaceutically acceptable salts thereof; wherein:

$R^1$ is an aromatic group, optionally condensed, optionally substituted with $R^B$ in one or more positions; a heteroaromatic group containing one or more heteroatoms, optionally substituted with $R^B$ or an indole group in one or more positions; a $C_{2-6}$ alkenylcarbonyl, optionally substituted with $R^B$ in one or more positions; a bicyclic aromatic, optionally substituted with $R^B$ in one or more positions, or a bicyclic heteroaromatic containing one or more heteroatoms, optionally substituted with $R^B$ in one or more positions;

$R^B$ is a halogen, hydroxy, nitrogen, cyano, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl;

$R^2$ is an aromatic group containing one or more heteroatoms, a heteroaromatic containing group containing one or more heteroatoms or methylene-3,4-dioxyphenyl groups, or a bicyclic aromatic containing one or more heteroatoms or methylene-3,4-dioxyphenyl groups;

$R^3$ is hydrogen, halogen, $C_{1-6}$ haloalkyl, $C_{1-3}$ heteroalkyl, or $C_{1-3}$ alkyl; and $R^4$ is hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl.

2. The compound of claim 1, or pharmaceutically acceptable salts thereof, wherein said compound is represented by formula (II):

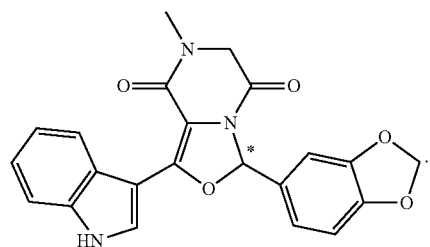
(II)

3. The compound of claim 2, or pharmaceutically acceptable salts thereof, wherein the compound is an (R)-isomer.

4. The compound of claim 2, or pharmaceutically acceptable salts thereof, wherein the compound is an (S)-isomer.

5. The compound of claim 1, or pharmaceutically acceptable salts thereof, wherein the compound is an (R)-isomer and represented by formula (Ib):

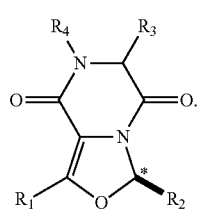
(Ib)

6. The compound of claim 1, or pharmaceutically acceptable salts thereof, wherein the compound is an (S)-isomer and represented by formula (Ic):

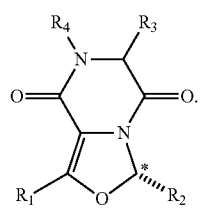
(Ic)

7. A pharmaceutical composition comprising an effective amount of one or more compounds of claim 1, or pharmaceutically acceptable salts thereof; and pharmaceutically acceptable excipients.

8. The pharmaceutical composition of claim 7, wherein the composition comprises a compound of formula (II):

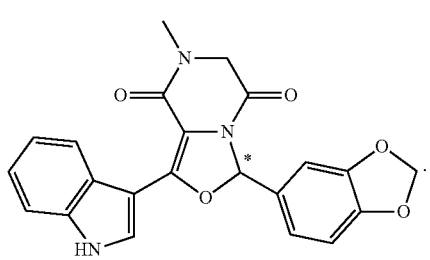
(II)

9. The pharmaceutical composition of claim 8, wherein the compound is an (R)-isomer and represented by formula (Ib):

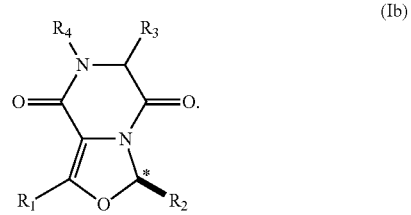
(Ib)

10. The pharmaceutical composition of claim 8, wherein the compound is an (S)-isomer and represented by formula (Ic):

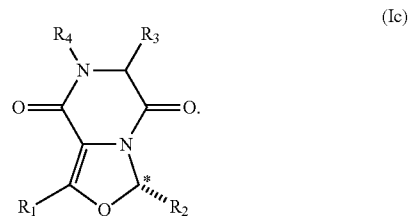
(Ic)

11. A method of inhibiting the enzymes phosphodiesterases in a patient, the method comprising administering the pharmaceutical composition of claim 7 to said patient.

12. A method of inhibiting the enzyme phosphodiesterase type 5 in a patient, the method comprising administering the pharmaceutical composition of claim 7 to said patient.

13. A method of inhibiting the enzymes phosphodiesterases in a patient, the method comprising administering the pharmaceutical composition of claim 8 to said patient.

14. A method of inhibiting the enzyme phosphodiesterase type 5 in a patient, the method comprising administering the pharmaceutical composition of claim 8 to said patient.

15. A method of preparing the compound of claim 2, the method comprising reacting compound 1

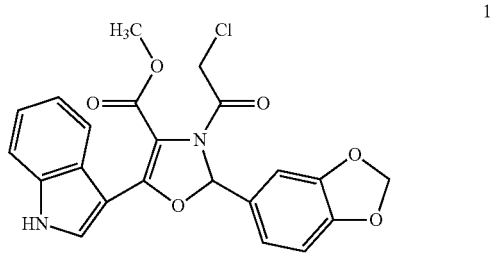
1 with methylamine in ethanol to provide compound 2

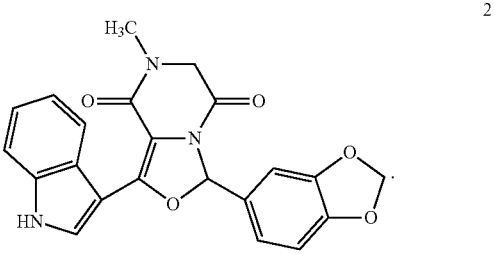
2

16. A method of preparing the compound of claim 2, the method comprising reacting compound 3
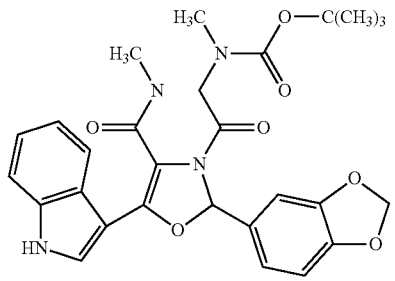
with hydrochloric acid in ethanol, followed by neutralization with sodium bicarbonate, to provide compound 2
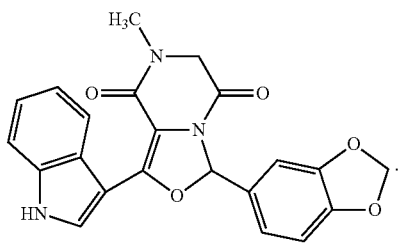
\* \* \* \* \*

UNITED STATES PATENT AND TRADEMARK OFFICE
CERTIFICATE OF CORRECTION

PATENT NO. : 8,338,432 B2  
APPLICATION NO. : 13/196363  
DATED : December 25, 2012  
INVENTOR(S) : Sacurai et al.

Page 1 of 1

It is certified that error appears in the above-identified patent and that said Letters Patent is hereby corrected as shown below:

On the Title Page, Item [54] and in the Specification, Column 1, line 1-4 please delete the current Title and replace with the following Title:

-- DERIVATIVES OF 6,7-DIHYDRO-3H-OXAZOLO[3,4,a]PYRAZINE-5,8-DIONE AS PDE-5 INHIBITORS --

Signed and Sealed this
Eighteenth Day of February, 2014

Michelle K. Lee
*Deputy Director of the United States Patent and Trademark Office*